United States Patent
Soerensen

(10) Patent No.: US 11,950,569 B2
(45) Date of Patent: Apr. 9, 2024

(54) ANIMAL CHEW TOY WITH DENTAL CARE COMPOSITION

(71) Applicant: Novozymes A/S, Bagsvaerd (DK)

(72) Inventor: Niels Henrik Soerensen, Skaevinge (DK)

(73) Assignee: Novozymes A/S, Bagsvaerd (DK)

( * ) Notice: Subject to any disclaimer, the term of this patent is extended or adjusted under 35 U.S.C. 154(b) by 921 days.

(21) Appl. No.: 16/611,658

(22) PCT Filed: May 8, 2018

(86) PCT No.: PCT/EP2018/061822
§ 371 (c)(1),
(2) Date: Nov. 7, 2019

(87) PCT Pub. No.: WO2018/206553
PCT Pub. Date: Nov. 15, 2018

(65) Prior Publication Data
US 2021/0137075 A1   May 13, 2021

(30) Foreign Application Priority Data

May 9, 2017   (EP) .................... 17170258

(51) Int. Cl.
*A01K 15/02*   (2006.01)
*A23K 50/40*   (2016.01)
*A61K 38/54*   (2006.01)

(52) U.S. Cl.
CPC ............ *A01K 15/026* (2013.01); *A23K 50/40* (2016.05); *A61K 38/54* (2013.01)

(58) Field of Classification Search
CPC ....... A01K 15/026; A23K 50/40; A61K 38/54
See application file for complete search history.

(56) References Cited

U.S. PATENT DOCUMENTS

| | | | | |
|---|---|---|---|---|
| 5,904,928 A | * | 5/1999 | Cyr ..................... | A23K 50/40 426/805 |
| 9,023,323 B2 | | 5/2015 | Trivedi et al. | |
| 2007/0081952 A1 | * | 4/2007 | Cardon ................. | A61Q 11/00 424/50 |
| 2009/0169677 A1 | | 7/2009 | Wittorff et al. | |
| 2011/0052661 A1 | | 3/2011 | Weiss | |

FOREIGN PATENT DOCUMENTS

| | | |
|---|---|---|
| RU | 2407512 | 12/2010 |
| WO | 1994005252 A1 | 3/1994 |
| WO | WO 2005/063184 * | 7/2005 |
| WO | 2014003307 A1 | 1/2014 |

OTHER PUBLICATIONS

Jakubovics, N. et al. Extracellular DNA in Oral Microbial Biofilms. Institut Pasteur 17:531-7, 2015. (Year: 2015).*
Hannig, C. et al. Efficacy of Enzymatic Toothpastes for Immobilisation of Protective Enzymes in the In situ Pellicle. Archives of Oral Biology 55(7)463-469, Jul. 2010. (Year: 2010).*
WO 2014-003307 A1—Database WPI Week AN 2014-A48396.
Gallagher, 2013, Letters in General Microbiology 1(16), 1-4.

* cited by examiner

Primary Examiner — Aaron J Kosar

(57) ABSTRACT

The invention provides an animal chew toy comprising a dental care composition, wherein the dental care composition comprises at least one peroxidase and at least one oxidase.

17 Claims, 1 Drawing Sheet

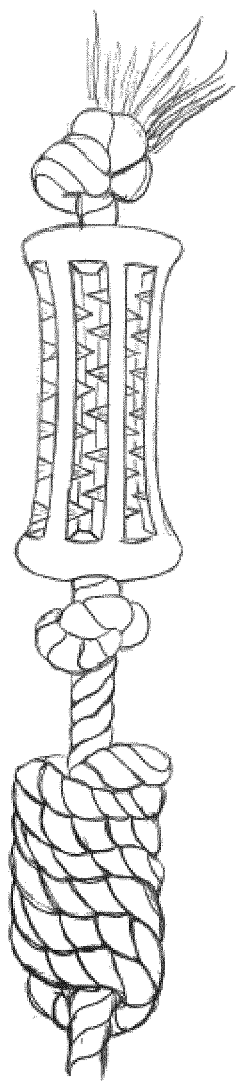

ANIMAL CHEW TOY WITH DENTAL CARE COMPOSITION

CROSS-REFERENCE TO RELATED APPLICATIONS

This application is a 35 U.S.C. 371 national application of PCT/EP2018/061822, filed May 8, 2018, which claims priority or the benefit under 35 U.S.C. 119 of European application no. 17170258.2, filed May 9, 2017. The contents of these applications are fully incorporated herein by reference.

FIELD OF THE INVENTION

The present invention relates to an animal chew toy comprising an enzymatic dental care composition, which is capable of improving oral hygiene by reducing bacterial proliferation.

BACKGROUND

Most dog owners never take a thorough look inside their dog's mouth. That is very unfortunate because it is estimated that over 80 percent of all dogs have severe oral problems. When the veterinarian meets the dog for vaccination it also often ends up in an investigation of the general health of the dog. Here the oral health is the most frequent cause for immediate action.

SUMMARY OF THE INVENTION

In a first aspect, the present invention provides an animal chew toy comprising a dental care composition, wherein the dental care composition comprises at least one peroxidase and at least one oxidase.

In another aspect is provided a kit of parts, comprising:
(a) a dental care composition comprising at least one peroxidase and at least one oxidase;
(b) an animal chew toy having an inner cavity or compartment suitable as a reservoir for the dental care composition of (a); and, optionally,
(c) instructions for use.

In other aspects are provided a method for preparing the animal chew toy of the first aspect, and a method for maintaining or improving the oral hygiene of an animal, and the use of an enzymatic dental care composition for maintaining or improving the oral hygiene of an animal.

Other aspects and embodiments of the invention are apparent from the following description.

BRIEF DESCRIPTION OF DRAWINGS

FIG. 1 illustrates the chew toy used in the Examples presented herein.

DETAILED DESCRIPTION

One of the most frequent issues with dogs from the age of three and up is their dental hygiene. The dog owners are asked to brush the teeth of the dog once or twice a day, but they rarely succeed doing that. This leads to very bad breath from the dog and severe dental problems later in the dog's life. A situation that demands anesthesia and extensive dental work by a veterinarian.

The oral hygiene of dogs and other animals is often an overseen issue. The puppy of the dog chews on everything it meets, and likes to investigate. However, this behavior changes as the dog becomes older, and the teeth, especially in the inner part of the oral cavity (the premolars and the molars), will often be the first to suffer from deposits of plaque and infection if the dog does not "exercise" them by chewing on bones and/or chew toys regularly. Keeping up this habit is very important for the health of the oral cavity.

The present invention provides a way of boosting the natural defenses of the oral cavity, while at the same time reducing or eliminating the malodors.

A dental care composition of the invention is added to and contained in a chew toy that releases the dental care composition while the dog chews on it. In addition, the chew toy has a mechanical effect on the established dental biofilm.

The chew toy is refilled with gel before given to the dog. This allows the dog to have up to two dental care sessions a day where it, so to speak, brushes its own teeth.

Thus, in another aspect, the invention provides a kit of parts, comprising:
(a) a dental care composition comprising at least one peroxidase and at least one oxidase;
(b) an animal chew toy having an inner cavity or compartment suitable as a reservoir for the dental care composition of (a); and, optionally,
(c) instructions for use.

The kit of parts may be in the form of a consumer product package, such as a cardboard or plastic box comprising parts (a), (b), and (c). Parts (a) and (b) are described in detail below and should be applied together to the animal, as described above.

In a preferred embodiment, the kit of parts comprises:
(a) a dental care composition comprising at least one peroxidase and at least one oxidase;
(b) an animal chew toy having an inner cavity or compartment suitable as a reservoir for the dental care composition of (a); and
(c) instructions for use.

Animal Chew Toy

A chew toy is a toy designed to be chewed by animals for purposes of stimulation and relief from boredom. The act of gnawing on a chew toy is meant to be soothing and to assist small animals, like puppies, in event of easing the pain when breaking in their adult teeth as the chewing process releases feel-good chemicals from the brain. There are several different types of chew toys, including rawhide, wood, paper and mineral. Chew toys are commonly associated with puppies and dogs, though they are also used for birds, rodents, and rabbits.

Chew toys are a vital part of a happy, healthy animal's life. In addition to providing hours of entertainment, they also allow the animal to work out anxiety and boredom by being occupied with chewing a toy. Chew toys also distract small animals from chewing on other "forbidden" items, and they assist in maintaining healthy teeth.

Preferred animal chew toys according to the invention are canine chew toys, and in particular dog chew toys.

Rawhide

Rawhide chew toys are most often associated with puppies and dogs, though rawhide toys are plentiful in the bird toy section of most pet stores. Rawhide is suitable for all animals except herbivores, as it is made of animal skin. Rabbits, which only eat vegetation, cannot have rawhide toys because their digestive systems cannot process them. This is a rather sturdy kind of chew toy and it can take months for a small animal or bird to destroy. Examples of rawhide chew toys are twists and rawhide bones.

Wood

Wood chew toys are made of a safe, non-poisonous, softer wood and are often coated in bright, vegetable-based dyes or paints. Wooden chew toys are given in place of the wood that small animals would find in the wild. They are a safe alternative for a small animal owner to purchase if the owner has no knowledge of the trees and shrubs growing in their area. They are generally used as either small rodents' toys or rabbit toys. Wooden chew toys help to keep teeth trimmed down, preventing eating difficulties in pets and unnecessary trips to a vet for teeth clipping.

Paper

Paper chew toys are made of non-bleached non-toxic paper. They are an inexpensive, or often free, option for small pet owners and can provide hours of stimulation and play for small animals. One common paper chew toy is an empty toilet paper tube. These can double as tunnels for very small rodents, and can also be used as modified piñatas for larger small animals.

Mineral

Mineral chew toys are made of flavored animal-safe minerals. These range from flavored fruit-shaped blocks for birds to ice-cream cone shaped mineral treats for rabbits. They also come shaped as bowls with fluffy minerals inside. A common mineral chew toy is the cuttlebone, a necessity in any bird's cage that helps to keep nails and beaks trimmed and healthy.

Rubber

There is a variety of rubber chew toys for dogs on the market that are molded into different shapes. Some of them are hollowed so that treats can be placed in them. This way, the dog has to "work" to get a treat. Rubber is a good chew toy for dogs but is unhealthy for small animals.

In order to ensure that the chew toy may be refilled with dental care composition, it is desired that the chew toy is made of a non-edible substance that is not meant to be ingested by the animal. Preferably, the animal chew toy consists entirely of primarily of a non-edible substance. Suitable non-edible substances include, but are not limited to, wood and rubber. In a preferred embodiment, the animal chew toy consists entirely or primarily of rubber.

Dental Care Composition

The dental care composition used in the animal chew toy of the invention comprises at least one peroxidase and at least one oxidase. The oxidase generates the hydrogen peroxide required by the peroxidase.

The dental care composition is preferably in the form of a gel or paste. Thus, the composition may include a viscosity regulating agent, such as a natural polymer.

Preferred natural polymers that may be used for regulating the viscosity include, but are not limited to, natural polymers selected from the group consisting of alginate, carrageenan, xanthan gum, guar gum, locust bean gum, and microcrystalline cellulose.

Preferably, the dental care composition is located on or at a surface of the animal chew toy. In a preferred embodiment, the dental care composition is located in or at an inner surface defining an inner cavity or compartment of the chew toy.

Preferably, the dental care composition is poured, squeezed or pressed into an inner cavity or compartment, which acts as a reservoir, of the animal chew toy, to sieve out when the animal chew on the toy. The form of the toy massages the gums and teeth of the animal, while the dental care composition comes out on the teeth of the animal.

Alternatively, the dental care composition is applied to and resides on an outer surface of the chew toy.

The animal chew toy or the dental care composition may comprise a flavoring agent to provide an attractive taste to the animal. Preferably, the flavoring agent tastes of a meat product. The flavoring agent may even be derived from a meat product. Such meat product may be chicken, pork, or beef.

Usually the dental care composition will also comprise a preservation agent, such as a sorbate or benzoate. The composition may also contain a coloring agent, preferably of natural origin, such as annatto red, β-carotene, etc.

Peroxidase

Peroxidases for use in the dental care composition are peroxidases according to EC 1.11.1.7, which are capable of oxidizing thiocyanate ($SCN^-$) to hypothiocyanous acid or hypothiocyanite, in the presence of hydrogen peroxide. Suitable peroxidases include, but are not limited to, lactoperoxidase, eosinophil peroxidase, myeloperoxidase and soybean peroxidase.

The thiocyanate which is oxidized by the peroxidase is naturally present in sufficient quantity in the oral cavity of animals. Alternatively, a small amount of a suitable thiocyanate salt can be added to the dental care composition.

A preferred peroxidase is lactoperoxidase, which is a natural component of colostrum and other types of milk. Accordingly, in a particular preferred embodiment of the invention, the dental care composition comprises colostrum or milk powder, or a fraction thereof containing lactoperoxidase.

Oxidase

The hydrogen peroxide for use with the peroxidase is produced by an oxidase. Examples of suitable oxidases include, but are not limited to, amino acid oxidase (see e.g., U.S. Pat. No. 6,248,575), lactate oxidase, galactose oxidase (see e.g., WO 00/50606), and various carbohydrate oxidases, such as glucose oxidase (see e.g., WO 95/29996) and hexose oxidase (see e.g., WO 99/31990).

By studying EC 1.1.3._, EC 1.2.3._, EC 1.4.3._, and EC 1.5.3._ or similar classes (under the International Union of Biochemistry), other examples of suitable oxidases and their corresponding substrates are easily recognized by one skilled in the art.

Many oxidases act on substrates that are naturally occurring in the oral cavity of (canine) animals, and such oxidases are the preferred oxidases for use in the invention.

Alternatively, the substrate may be added to the dental care composition, either directly or indirectly. An example of an indirect supply of substrate is the use of a carbohydrase to degrade naturally occurring polysaccharides or oligosaccharides into carbohydrate oxidase substrates, such as glucose and other hexoses.

The dental care composition may include a carbohydrase, which is capable of supplying a suitable carbohydrate as a substrate to a carbohydrate oxidase.

A preferred carbohydrase is a glucan 1,4-alpha-glucosidase (EC 3.2.1.3), which is also known as glucoamylase or amyloglucosidase.

Nuclease In addition to at least one peroxidase and at least one oxidase, the dental care composition may also comprise additional enzymes able to degrade dental biofilms or components thereof. In particular, the dental composition may comprise one or more nucleases. A nuclease is any enzyme that catalyzes the hydrolytic cleavage of phosphodiester linkages in DNA and/or RNA backbones, thereby removing DNA and/or RNA.

Preferably, the nuclease is a DNAse. DNases suitable for use with the present invention include those described, e.g., in WO 2017/060475, WO 2014/087011, WO 2015/155350 and WO 2015/155351.

Preferred DNases may be obtained from *Bacillus*, preferably *Bacillus cibi, Bacillus horikoshii, Bacillus licheniformis, Bacillus subtilis, Bacillus horneckiae, Bacillus idriensis, Bacillus algicola, Bacillus vietnamensis, Bacillus hwajinpoensis, Bacillus indicus, Bacillus marisflavi* or *Bacillus luciferensis*. In a preferred embodiment, the DNAse is obtained from *Bacillus cibi*.

Preferred DNases may also preferably be fungal. Particularly preferred are DNases obtained from *Aspergillus* sp., in particular *Aspergillus oryzae*, or from *Trichoderma* sp., in particular *Trichoderma harzianum*.

Lysozyme

The dental care composition may also comprise one or more lysozymes or lysozyme variants. Lysozyme is also known as muramidase and occurs naturally in many organisms such as viruses, plants, insects, birds, reptiles, and mammals. In mammals, lysozyme has been isolated from nasal secretions, saliva, tears, intestinal content, urine and milk. The enzyme cleaves the glycosidic bond between carbon number 1 of N-acetylmuramic acid and carbon number 4 of N-acetyl-D-glucosamine. In vivo, these two carbohydrates are polymerized to form the cell wall polysaccharide of many microorganisms. Due to its ability to degrade bacterial peptidoglycans, lysozyme functions as an antibacterial agent.

Lysozyme has been classified into five different glycoside hydrolase (GH) families (CAZy, www.cazy.org): hen egg-white lysozyme (GH22), goose egg-white lysozyme (GH23), bacteriophage T4 lysozyme (GH24), *Sphingomonas* flagellar protein (GH73) and Chalaropsis lysozymes (GH25). Lysozymes from the families GH23 and GH24 are primarily known from bacteriophages and have recently been identified in fungi. The lysozyme family GH25 has been found to be structurally unrelated to the other lysozyme families. Lysozyme extracted from hen egg white is the primary product available on the commercial market.

For the present invention, preferred lysozymes may be selected from GH22 lysozymes, GH23 lysozymes, GH24 lysozymes, GH73 lysozymes, and GH25 lysozymes. Preferably, the lysozyme is a GH25 lysozyme. Examples of GH25 lysozymes can be found in, e.g., WO 2013/076253, WO 2005/080559, PCT/CN2017/117753, and PCT/CN2017/117765.

Oral Hygiene

Poor oral hygiene results in infected gums, rotting tooth sockets and loose teeth. The dog has often a foul odor from the breath (halitosis) as a result of generalized periodontitis. Bad breath is just a minor part of a much more noxious disease process. Diseases originating from the poor hygiene of the mouth may even reduce the lifespan of the dog.

The following oral diseases are the result of insufficient oral hygiene, all of which are easily recognized by visual inspection of the oral cavity:

Gingivitis—inflammation of the gums.
Periodontitis—a general term for a disease of the oral cavity that attacks the gum and bone and delicate tissues around the teeth.
Pyorrhea—inflammation of the gums and tooth sockets, often leading to loosening of the teeth and accompanied by pus.
Plaque—the first buildup of material adhering to tooth enamel. Composed of a mix of intercellular matrix of bacteria, salivary polymers, remnants of epithelial cells and white blood cells, it can cause caries, calculi buildup and periodontal disease.

An indirect measurement of poor oral hygiene is halitosis (bad breath), which can be evaluated by measuring the production of volatile sulfur compounds (VSC) responsible for halitosis. This is described in Hennet et al., "Oral malodor measurements on a tooth surface of dogs with gingivitis", Am J Vet Res., 1998 March, 59(3), pp. 255-257.

The invention is further described in the following list of embodiments:

Embodiment 1. An animal chew toy comprising a dental care composition, wherein the dental care composition comprises at least one peroxidase and at least one oxidase.

Embodiment 2. The animal chew toy of embodiment 1, wherein the dental care composition is located on or at a surface of the animal chew toy.

Embodiment 3. The animal chew toy of any of embodiments 1-2, wherein the dental care composition is located in or at an inner cavity or compartment of the animal chew toy.

Embodiment 4. The animal chew toy of any of embodiments 1-3, wherein the at least one peroxidase is capable of oxidizing thiocyanate (SCN⁻) to hypothiocyanous acid or hypothiocyanite; or the at least one peroxidase is a lactoperoxidase.

Embodiment 5. The animal chew toy of any one of embodiments 1-4 wherein the dental care composition further comprises colostrum or milk powder.

Embodiment 6. The animal chew toy of any one of embodiments 1-5, wherein the at least one oxidase is a carbohydrate oxidase.

Embodiment 7. The animal chew toy of any one of embodiments 1-6, wherein the at least one oxidase is a hexose oxidase.

Embodiment 8. The animal chew toy of any one of embodiments 1-7, wherein the at least one oxidase is a glucose oxidase.

Embodiment 9. The animal chew toy of any one of embodiments 1-8, wherein the dental care composition further comprises at least one glucan 1,4-alpha-glucosidase.

Embodiment 10. The animal chew toy of any of embodiments 1-9, wherein the dental care composition further comprises at least one nuclease; preferably the at least one nuclease is a DNAse; more preferably the at least one nuclease is a DNAse obtained from *Bacillus cibi, Bacillus horikoshii, Bacillus licheniformis, Bacillus subtilis, Bacillus horneckiae, Bacillus idriensis, Bacillus algicola, Bacillus vietnamensis, Bacillus hwajinpoensis, Bacillus indicus, Bacillus marisflavi* or *Bacillus luciferensis*.

Embodiment 11. The animal chew toy of any of embodiments 1-10, wherein the dental care composition further comprises at least one lysozyme; preferably the at least one lysozyme is a GH22 lysozyme, GH23 lysozyme, GH24 lysozyme, GH73 lysozyme, or GH25 lysozyme; more preferably the at least one lysozyme is a GH25 lysozyme.

Embodiment 12. The animal chew toy of any one of embodiments 1-11, wherein the dental care composition is in the form of a gel or paste.

Embodiment 13. The animal chew toy of any one of embodiments 1-12, wherein the dental care composition further comprises a viscosity regulating agent.

Embodiment 14. The animal chew toy of embodiment 13, wherein the viscosity regulating agent is a natural polymer.

Embodiment 15. The animal chew toy of embodiment 14, wherein the viscosity regulating agent is selected from the group consisting of alginate, carrageenan, xanthan gum, guar gum, locust bean gum, and microcrystalline cellulose.

Embodiment 16. The animal chew toy of any one of embodiments 1-15, which further comprises a flavoring agent.

Embodiment 17. The animal chew toy of embodiment 16, wherein the flavoring agent is comprised in the dental care composition.

Embodiment 18. The animal chew toy of embodiment 16 or 17, wherein the flavoring agent tastes of a meat product, such as chicken, pork, or beef.

Embodiment 19. The animal chew toy of any one of embodiments 1-18, wherein the animal is a canine animal.

Embodiment 20. The animal chew toy of any one of embodiments 1-19, wherein the animal is a dog.

Embodiment 21. A kit of parts, comprising:
(a) a dental care composition comprising at least one peroxidase and at least one oxidase;
(b) an animal chew toy having an inner cavity or compartment suitable as a reservoir for the dental care composition of (a); and, optionally,
(c) instructions for use.

Embodiment 22. The kit of parts of embodiment 21, which is a consumer product package.

Embodiment 23. The kit of parts of embodiment 21 or 23, which is in the form of a cardboard or plastic box.

Embodiment 24. The kit of parts of any one of embodiments 21-23, wherein the at least one peroxidase is capable of oxidizing thiocyanate ($SCN^-$) to hypothiocyanous acid or hypothiocyanite; or the at least one peroxidase is a lactoperoxidase.

Embodiment 25. The kit of parts of any one of embodiments 21-24, wherein the dental care composition further comprises colostrum or milk powder.

Embodiment 26. The kit of parts of any one of embodiments 21-25, wherein the at least one oxidase is a carbohydrate oxidase.

Embodiment 27. The kit of parts of any one of embodiments 21-26, wherein the at least one oxidase is a hexose oxidase.

Embodiment 28. The kit of parts of any one of embodiments 21-27, wherein the at least one oxidase is a glucose oxidase.

Embodiment 29. The kit of parts of any one of embodiments 21-28, wherein the dental care composition further comprises at least one glucan 1,4-alpha-glucosidase.

Embodiment 30. The kit of parts of any one of embodiments 21-29, wherein the dental care composition further comprises at least one nuclease; preferably the at least one nuclease is a DNAse; more preferably the at least one nuclease is a DNAse obtained from *Bacillus cibi, Bacillus horikoshii, Bacillus licheniformis, Bacillus subtilis, Bacillus horneckiae, Bacillus idriensis, Bacillus algicola, Bacillus vietnamensis, Bacillus hwajinpoensis, Bacillus indicus, Bacillus marisflavi* or *Bacillus luciferensis*.

Embodiment 31. The kit of part of any of embodiments 21-30, wherein the dental care composition further comprises at least one lysozyme; preferably the at least one lysozyme is a GH22 lysozyme, GH23 lysozyme, GH24 lysozyme, GH73 lysozyme, or GH25 lysozyme; more preferably the at least one lysozyme is a GH25 lysozyme.

Embodiment 32. The kit of parts of any one of embodiments 21-31, wherein the dental care composition is in the form of a gel or paste.

Embodiment 33. The kit of parts of any one of embodiments 21-32, wherein the dental care composition further comprises a viscosity regulating agent.

Embodiment 34. The kit of parts of embodiment 33, wherein the viscosity regulating agent is a natural polymer.

Embodiment 35. The kit of parts of embodiment 34, wherein the viscosity regulating agent is selected from the group consisting of alginate, carrageenan, xanthan gum, guar gum, locust bean gum, and microcrystalline cellulose.

Embodiment 36. The kit of parts of any one of embodiments 21-35, wherein the dental care composition or the animal chew toy comprises a flavoring agent.

Embodiment 37. The kit of parts of any one of embodiments 21-36, wherein the dental care composition comprises a flavoring agent.

Embodiment 38. The kit of parts of embodiment 36 or 37, wherein the flavoring agent tastes of a meat product, such as chicken, pork, or beef.

Embodiment 39. The kit of parts of any one of embodiments 21-38, wherein the animal is a canine animal.

Embodiment 40. The kit of parts of any one of embodiments 21-39, wherein the animal is a dog.

Embodiment 41. A method for preparing the animal chew toy of any one of embodiments 1-20, comprising combining (a) and (b) of the kit of parts of any one of embodiments 21-40.

Embodiment 42. A method for maintaining or improving the oral hygiene of an animal, comprising the animal chewing on the animal chew toy of any one of embodiments 1-20, wherein the oral cavity of the animal is contacted with the dental care composition.

Embodiment 43. Use of a dental care composition for maintaining or improving the oral hygiene of an animal, wherein the dental care composition comprises at least one peroxidase and at least one oxidase.

Embodiment 44. The use according to embodiment 43, wherein the at least one peroxidase is capable of oxidizing thiocyanate ($SCN^-$) to hypothiocyanous acid or hypothiocyanite; or the at least one peroxidase is a lactoperoxidase.

Embodiment 45. The use according to embodiment 43 or 44, wherein the dental care composition further comprises colostrum or milk powder.

Embodiment 46. The use according to any one of embodiments 43-45, wherein the at least one oxidase is a carbohydrate oxidase.

Embodiment 47. The use according to any one of embodiments 43-46, wherein the at least one oxidase is a hexose oxidase.

Embodiment 48. The use according to any one of embodiments 43-47, wherein the at least one oxidase is a glucose oxidase.

Embodiment 49. The use according to any one of embodiments 43-48, wherein the dental care composition further comprises at least one glucan 1,4-alpha-glucosidase.

Embodiment 50. The use according to any one of embodiments 43-49, wherein the dental care composition further comprises at least one nuclease; preferably the at least one nuclease is a DNAse; more preferably the at least one nuclease is a DNAse obtained from *Bacillus cibi, Bacillus horikoshii, Bacillus licheniformis, Bacillus subtilis, Bacillus horneckiae, Bacillus idriensis, Bacillus algicola, Bacillus vietnamensis, Bacillus hwajinpoensis, Bacillus indicus, Bacillus marisflavi* or *Bacillus luciferensis*.

Embodiment 51. The use according to any one of embodiments 43-50, wherein the dental care composition further comprises at least one lysozyme; preferably the at least one lysozyme is a GH22 lysozyme, GH23 lysozyme, GH24 lysozyme, GH73 lysozyme, or GH25 lysozyme; more preferably the at least one lysozyme is a GH25 lysozyme.

Embodiment 52. The use according to any one of embodiments 43-51, wherein the dental care composition is in the form of a gel or paste.

Embodiment 53. The use according to any one of embodiments 43-52, wherein the dental care composition further comprises a viscosity regulating agent.

Embodiment 54. The use according to embodiment 53, wherein the viscosity regulating agent is a natural polymer.

Embodiment 55. The use according to embodiment 54, wherein the viscosity regulating agent is selected from the group consisting of alginate, carrageenan, xanthan gum, guar gum, locust bean gum, and microcrystalline cellulose.

Embodiment 56. The use according to any one of embodiments 43-55, wherein the dental care composition further comprises a flavoring agent.

Embodiment 57. The use according to embodiment 56, wherein the flavoring agent tastes of a meat product, such as chicken, pork, or beef.

Embodiment 58. The use according to any one of embodiments 43-57, wherein the animal is a canine animal.

Embodiment 59. The use according to any one of embodiments 43-58, wherein the animal is a dog.

EXAMPLES

Example 1

Effects of Dental Care Composition on Animal Activity

Purpose:
To investigate whether addition of a dental care composition of the invention increases a dog's willingness to play and interact with a chew toy.
Test Population:
28 dogs, each weighing at least 15 kg.
Dental Care Composition:
For the preparation of 100 kg dental care composition, an Avicel stock gel (ingredients: 53.5 kg cold tap water; 0.1 kg potassium sorbate; 2.2 kg Avicel-plus GP 7315, FMC/Dupont) was initially prepared and activated by high-shear mixing. The final dental care composition was prepared by mixing of the Avicel stock gel and the remaining ingredients (Table 1) at room temperature.

TABLE 1

Dental care composition ingredients.

| Gel ingredients | Vendor | kg |
|---|---|---|
| Lactose free SMP* | Valio Elia | 10.0 |
| CMC, Type AMD 134 | DuPont | 0.05 |
| Sorbitol powder | | 10.0 |
| Carnad Chicken powder LS | Carnad A/S | 10.0 |
| AMG (AMG 300 L) | Novozymes A/S | 0.30 |
| GOX (Novozym 39199) | Novozymes A/S | 0.11 |
| Glycerol (>99.5%) | | 12.0 |
| Alginate, Protanal GP 3350 | FMC/DuPont | 1.0 |
| Citric acid, adjust to pH 5.5 | | 0.40 |

(*Contains active lactoperoxidase).

Test Setup:
A commercially available red and yellow rope and plastic tug toy as depicted in FIG. 1 was used for the tests.

The test room was a minimum furnished room with one table and two chairs with natural daylight, approximately 10 square meters of open space for testing and free movement.

Test personnel were all wearing neutral white shirts and were not wearing heavy perfume.

Full tests were video recorded for documentation purposes and manually scored while test was ongoing.

Test Protocol:
1. Owner and dog were allowed to enter the room and the dog was given 3-5 minutes while close to its owner in order to familiarize with the test personnel and acclimatize to the room while the owner was interviewed
2. Dog was introduced to the chew toy without dental care composition added, and the dog's interest and activity (licking and chewing) was recorded for a maximum of 3 minutes.
3. 1.5 ml of dental care composition was applied to the chew toy using a syringe, and activity (licking, chewing, and playfulness) was recorded for a maximum of 5 minutes and compared by test personnel and owner to the activity level prior to addition of the dental care composition.
Results:
Table 2 shows the activity of the dogs before and after addition of the dental care compositions to the chew toy.

TABLE 2

Dog activity before and after addition of the gel.

| Activity | Before addition of dental care composition | After addition of dental care composition |
|---|---|---|
| Licking | 0 | 24 |
| Chewing | 2 | 18 |
| No interaction | 4 | 4 |

None of the dogs tested reacted negatively to addition of the dental care composition to the chew toy. 4 out of 28 dogs were disinclined to participate in the test due to owner-perceived mood or nervousness. Overall, addition of the dental care composition highly increased the activity of the dog and the interaction with the toy.

The invention claimed is:
1. A dental care composition for maintaining or improving the oral hygiene of an animal, wherein the dental care composition comprises at least one peroxidase, at least one oxidase, and one or more of colostrum and milk powder.
2. The dental care composition of claim 1, wherein the at least one peroxidase is a lactoperoxidase.
3. The dental care composition of claim 1, wherein the at least one oxidase is a carbohydrate oxidase.
4. The dental care composition of claim 1, further comprising at least one glucan 1,4-alpha-glucosidase.
5. The dental care composition of claim 1, further comprising at least one nuclease.
6. The dental care composition of claim 5, wherein the at least one nuclease is a DNAse obtained from *Bacillus cibi*, *Bacillus horikoshii*, *Bacillus licheniformis*, *Bacillus subtilis*, *Bacillus horneckiae*, *Bacillus idriensis*, *Bacillus algicola*, *Bacillus vietnamensis*, *Bacillus hwajinpoensis*, *Bacillus indicus*, *Bacillus marisflavi* or *Bacillus luciferensis*.
7. The dental care composition of claim 1, further comprising at least one lysozyme.
8. The dental care composition of claim 7, wherein the at least one lysozyme is a GH22 lysozyme, GH23 lysozyme, GH24 lysozyme, GH73 lysozyme or GH25 lysozyme.
9. The dental care composition of claim 1, further comprising a viscosity regulating agent.
10. The dental care composition of claim 9, wherein the viscosity regulating agent is selected from alginate, carrageenan, xanthan gum, guar gum, locust bean gum and microcrystalline cellulose.
11. The dental care composition of claim 1, further comprising a flavoring agent.

12. An animal chew toy comprising the dental care composition of claim 1.

13. The animal chew toy of claim 12, which is suitable for canine animals.

14. The animal chew toy of claim 12, wherein the dental care composition is located in or at an inner cavity or compartment of the animal chew toy.

15. A method for maintaining or improving the oral hygiene of an animal, comprising contacting the oral cavity of said animal with the dental care composition of claim 1.

16. A method for maintaining or improving the oral hygiene of an animal, applying the dental care composition of claim 1 to an animal chew toy.

17. The method of claim 16, wherein the dental care composition of claim 1 is introduced into an inner cavity or compartment of said animal chew toy.

* * * * *